(12) United States Patent
Kaneko (10) Patent No.: US 11,468,560 B2
(45) Date of Patent: Oct. 11, 2022

(54) HEAD-IMAGE EVALUATION APPARATUS AND HEAD-IMAGE EVALUATION METHOD

(71) Applicant: Aventino, Inc., Yokohama (JP)

(72) Inventor: Akiko Kaneko, Yokohama (JP)

(73) Assignee: Aventino, Inc., Yokohama (JP)

( * ) Notice: Subject to any disclaimer, the term of this patent is extended or adjusted under 35 U.S.C. 154(b) by 248 days.

(21) Appl. No.: 16/626,567

(22) PCT Filed: Nov. 5, 2018

(86) PCT No.: PCT/JP2018/040986
§ 371 (c)(1),
(2) Date: Dec. 26, 2019

(87) PCT Pub. No.: WO2019/093266
PCT Pub. Date: May 16, 2019

(65) Prior Publication Data
US 2020/0143535 A1    May 7, 2020

(30) Foreign Application Priority Data

Nov. 7, 2017   (JP) .............................. JP2017-214403

(51) Int. Cl.
*G06T 7/00*        (2017.01)
*A61B 5/107*       (2006.01)
*A61B 5/00*        (2006.01)

(52) U.S. Cl.
CPC .......... *G06T 7/0012* (2013.01); *A61B 5/1072* (2013.01); *A61B 5/448* (2013.01); *G06T 2207/30004* (2013.01)

(58) Field of Classification Search
CPC ......... G06T 7/0012; G06T 2207/30004; A61B 5/1072; A61B 5/448
See application file for complete search history.

(56) References Cited

U.S. PATENT DOCUMENTS

2010/0106679 A1   4/2010  Yamaguchi et al.

FOREIGN PATENT DOCUMENTS

JP      H04-105045 A         4/1992
JP      2002360545 A    *   12/2002
(Continued)

OTHER PUBLICATIONS

NPL "Follicular miniaturization in female pattern hair loss: clinicopathological correlations" A.G. Messenger and R. Sinclair* (Year: 2006).*

(Continued)

*Primary Examiner* — Vu Le
*Assistant Examiner* — Winta Gebreslassie
(74) *Attorney, Agent, or Firm* — Yokoi & Co., U.S.A.; Toshiyuki Yokoi (57) ABSTRACT

A purpose of the present invention is to categorize various shapes in early FPHL and to define progression classification in order to determine the progress and the therapeutic effect.

A head-image evaluation apparatus includes an acquiring unit 250 that acquires a head image 80 obtained by photographing the hair of a subject, a recognizing unit 260 that recognizes, from a reflection image 100 in which surface-reflected light in the head image 80 is formed, the shape of the surface-reflected light, and a categorizing unit 270 that determines a shift degree of the shape of the surface-reflected light from the reflection image 100 with image processing, and categorizes the degree as any one of a plurality of stages 280.

4 Claims, 11 Drawing Sheets

(56) References Cited

FOREIGN PATENT DOCUMENTS

| JP | 2008-206975 A | 9/2008 |
|---|---|---|
| WO | 2017/057835 A | 4/2017 |

OTHER PUBLICATIONS

International Search Report for PCT/JP2018/040986 dated Jan. 22, 2019.
PCT written opinion dated Jan. 22, 2019.
Erich Ludwig, Classification of the types of *androgenetic alopecia* (common baldness) occurring in the female sex, British Journal of Dermatology, pp. 247-254, Mar. 21, 1977.
Elise A. Olsen, The midline part: an important physical clue to the clinical diagnosis of androgenetic alopecia in women, Journal of the American Academy of Dermatology, pp. 106-109, Jan. 1999.
Elise A. Olsen, Female pattern hair loss, Journal of the American Academy of Dermatology, pp. S70-S80, Sep. 2001.
M. Harries, et al., Towards a consensus on how to diagnose and quantify female pattern hair loss—The 'Female Pattern Hair Loss Severity Index (FPHL-SI)', Journal of European Academy of Dermatology and Venereology, pp. 667-676, Apr. 2016.
S. Biondo, et al., Women who present with female pattern hair loss tend to underestimate the severity of their hair loss, British Journal of Dermatology, pp. 750-752, Apr. 2004.
Ulrike Blume-Peytavi, et al., A randomized, single-blind trial of 5% minoxidil foam once daily versus 2% minoxidil solution twice daily in the treatment of androgenetic alopecia in women, Journal of the American Academy of Dermatology, pp. 1126-1134, Dec. 2011.
Takashi Itou, et al., Structural analysis of human hair fibers by micro-beam SAXS and application to the development of haircare products, Journal of JSSRR, pp. 80-86, Mar. 2008.
Rie Ueki, The Health of Hair: Prducing Beatiful Hair, Juntendo Medical Journal, pp. 327-330, Aug. 2013.

* cited by examiner

Grade 1

Grade 4       Grade 5

HEAD-IMAGE EVALUATION APPARATUS AND HEAD-IMAGE EVALUATION METHOD

TECHNICAL FIELD

The present invention relates to an evaluation apparatus and an evaluation method for evaluating hair loss based on a hair image.

BACKGROUND ART

Female pattern hair loss (FPHL) is diffuse alopecia that occurs mainly in women. As FPHL pattern classification, Ludwig presented the three-stage classification in 1977 into (see Non-Patent Literature 1), and Olsen presented the Christmastree pattern in 1999 (see Non-Patent Literature 2). With these pattern classifications, the shape of FPHL that has advanced to some extent can be evaluated, but the classifications are based on the size of exposed scalp that is only observed in an advanced stage, and are not useful for evaluating early female pattern hair loss (early FPHL). Early FPHL means a condition of being mild in FPHL, and Olsen expressed the feature as "a slightly opened partline" (see Non-Patent Literature 3).

On the other hand, Sinclair et al. considered early FPHL, that is the feature of appearance in a condition of being mildest, as "no change in a partline" (see Non-Patent Literature 5). As described, early FPHL has various symptoms in a condition of being mild, and the definition of "early" in FPHL varies depending on experts. Thus, although early FPHL has various symptoms in a condition of being mild, all the early FPHL types are classified as one type.

There has been no evaluation method for finely classifying various symptoms in early FPHL. Although there is a therapeutic effect evaluation for FPHL using a photograph of a whole of the hair (global photograph: GP), the seven-point scale has been mainly used. In the seven-point scale, a GP before treatment is set as a base line, and the impression of change from the base line is evaluated as one of seven stages (−3=significantly reduced, −2=fairly reduced, −1=slightly reduced, 0=unchanged, +1=slightly improved, +2=fairly improved, +3=significantly improved). However, the evaluation between a patient and a medical doctor/researcher does not necessarily match (see Non-Patent Literature 6).

In daily medical examination, GPs have been used as a method for the classifying the severity and determining the therapeutic effect in male pattern hair loss. In FPHL, Olsen referred to GPs as an evaluation item that is the most important and has the credibility in the FPHL clinical study. However, early FPHL patients rarely have opened partlines or scalp seen through hair, and it is difficult to evaluate the degree with GPs using the existing FPHL classification. This is one of unsolved problems in treatment for early FPHL.

CITATION LIST

Non-Patent Literature

Non-Patent Literature 1: Ludwig E. Classification of the types of androgenetic alopecia (common baldness) occurring in the female sex. Br J Dermatol. 1977 September; 97(3): 247-54

Non-Patent Literature 2: Olsen E A. The midline part: an important physical clue to the clinical diagnosis of androgenetic alopecia in women. J Am Acad Dermatol. 1999 January; 40 (1): 106-9

Non-Patent Literature 3: Olsen E A. Female pattern hair loss J Am Acad Dermatol 2001 September; 45 (3 Suppl): S70-80

Non-Patent Literature 4: Harries M, Tosti A, Bergfeld W, Blume-Peytavi U, ShapiroJ, Lutz G, Messenger A, Sinclair R, Paus R. Towards a consensus on how to diagnose and quantify female pattern hair loss—The 'Female Pattern Hair Loss Severity Index (FPHL-SI)'. J Eur Acad Dermatol Venereol. 2016 April; 30 (4): 667-76

Non-Patent Literature 5: Biondo S, Goble D, Sinclair R. Women who present with female pattern hair loss tend to underestimate the severity of their hair loss. Br J Dermatol. 2004 April; 150(4):750-2.

Non-Patent Literature 6: Blume-Peytavi Ul, Hillmann K, Dietz E, Canfield D, Garcia Bartels N. A randomized, single-blind trial of 5% minoxidil foam once daily versus 2% minoxidil solution twice daily in the treatment of androgenetic alopecia in women. J Am Acad Dermatol. 2011 December; 65 (6): 1126-1134

SUMMARY OF INVENTION

Technical Problem

Thus, one of problems of early FPHL is how to objectively evaluate the degree of hair loss (decrease in the hair volume of the head) of which a patient is aware and to determine the therapeutic effect (see Non-Patent Literature 4). Since a patient in early FPHL has more chances to recover with appropriate therapeutic intervention than in FPHL that has advanced, to start treatment in an early FPHL stage has significance in increasing the therapeutic effect and in reducing the emotional and financial burdens on the patient. For this reason, it is required to provide an evaluation method capable of categorizing early FPHL having various symptoms despite a mild degree, finely classifying progression, and determining the therapeutic effect.

Solution to Problem

A head-image evaluation apparatus according to the present embodiment includes an acquiring unit that acquires a head image obtained by photographing the hair of a subject, a recognizing unit that recognizes, from a reflection image in which surface-reflected light in the head image is formed, the shape of the surface-reflected light, and a categorizing unit that determines a distortion degree of the shape of the surface-reflected light in the reflection image with image processing, and categorizes the distortion degree as one of a plurality of stages.

Advantageous Effects of Invention

In the present embodiment, by evaluating the degree of hair loss or determining the therapeutic effect with GPs, it is possible to obtain a beneficial result for both a medical practitioner and a patient to decide a treatment policy in early hair loss represented by early FPHL. With the present embodiment, it is possible to establish suitable progression classification for early hair loss represented by early FPHL and to determine the therapeutic effect. Thus, it is possible to increase chances to recover with appropriate therapeutic intervention, and to treat hair loss in an early stage, which has been desired.

By setting evaluation criteria based on the shape of surface-reflected light, it is possible to evaluate treatment progress with GPs even in early FPHL that is difficult to evaluate objectively. The evaluation method using GPs according to the present embodiment is easily utilized by medical practitioners and helps patients to easily understand the progress, and is useful as an evaluation method for an early stage of hair loss, such as early FPHL.

With a GP evaluation method according to the present embodiment, patients easily understand fine gradual change in an early FPHL stage. With the GP evaluation method according to the present embodiment, it is possible to grasp a sign of change in the hair before an obvious change occurs. In FPHL, factors that affect the change in the hair cycle that is the FPHL disease mechanism are complicated, the process is not uniform, and remission or aggravation can happen. By detecting a sign of change in an early stage using the GP evaluation method according to the present embodiment, a treatment policy is easily decided, which helps treatment for hair loss, such as mainly early FPHL.

DESCRIPTION OF EMBODIMENTS

[Outline]

In the present embodiment, changes in surface-reflected light of flash light/strobe light generated on the hair when GPs are photographed are focused, and the degree of early hair loss, such as mainly early FPHL, is finely classified based on the difference in the shape of the surface-reflected light in order to evaluate the degree and the therapeutic effect.

The inventor presumed that various patterns in early FPHL were caused by three-dimensional factors formed by the hair diameter, hair density, hair elasticity, and the like, as a predisposition, that is, change in the thickness. Although a decrease in the hair volume that is the core of early FPHL is a three-dimensional change in the thickness, a new index other than the exposure degree of scalp is required to evaluate such a change with two-dimensional GPs. The inventor focused on changes in surface-reflected light of flash light generated on the hair when GPs were photographed, and devised a degree evaluation method using GPs of early hair loss, such as mainly early FPHL, and based on reflection patterns of flash light.

The surface-reflected light is shining light reflected on the cuticle surface of the hair. The quality of the light belt varies depending on the color of the hair or damage of the cuticle, and is also changed by the volume of the hair. When the whole of the head is photographed from the parietal region direction, surface-reflected light appears on the ridgeline obtained by connecting the highest points of the thickness of the hair in the vertical direction at regions of the head.

Thus, changes in the volume from early FPHL to a normal condition are classified, based on the features of surface-reflected light in GPs, into five stages. The hair on the surface of the head curves from the midline to the outer sides (ears), and some hair exposed from the surface with angles curves by its weight and overlaps as it lengthens. If the hair is parted at the center, the position at which surface-reflected light is generated is determined depending on the degree of hair overlapping and the curve of the head.

[Configuration]

Figure 1:
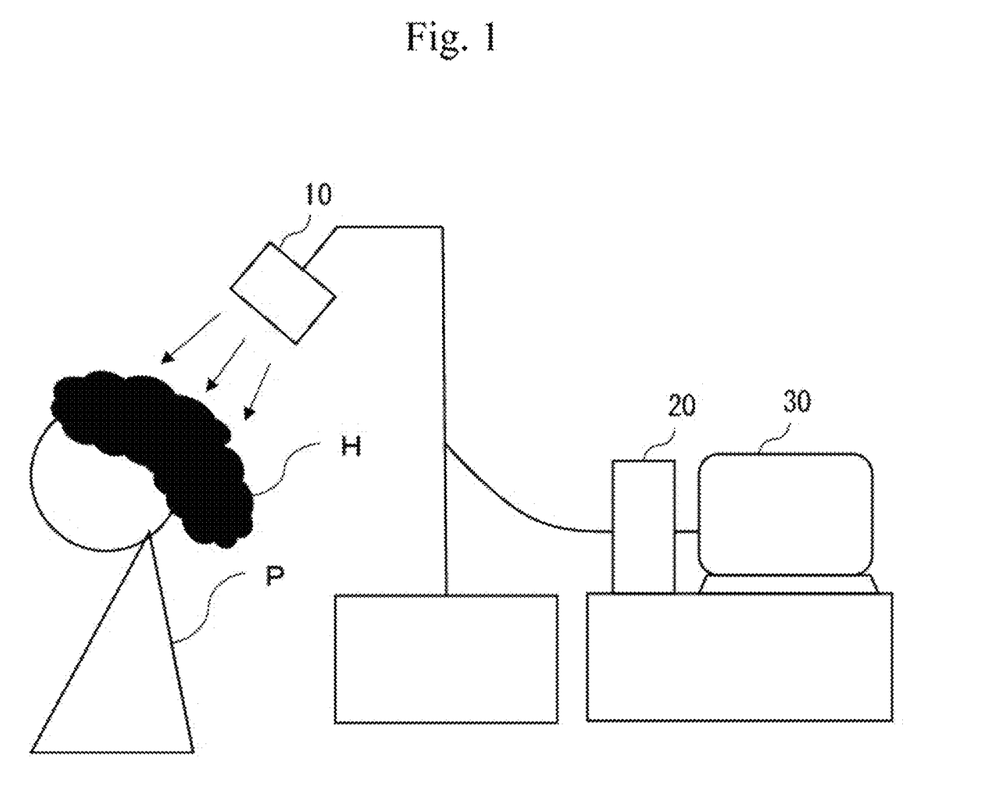
FIG. 1 is a diagram showing a configuration of an entire system including photographing a head image according to the present embodiment.

FIG. 1 is a diagram showing a configuration of an entire system including photographing a head image according to the present embodiment. This evaluation system includes an imaging unit 10 and an evaluation apparatus 20. The imaging unit 10 includes a stroboscope that emits flash light. The imaging unit 10 photographs hair H of a subject P. The image photographed by the imaging unit 10 is input to the evaluation apparatus 20, and image evaluation processing is performed. The evaluation apparatus 20 acquires and evaluates the head image.

(Hardware Configuration of Imaging Unit 10)

The imaging unit 10 includes an imaging device, such as a CCD or complementary metal oxide semiconductor (CMOS), and generates and outputs an image signal of an object imaged on the imaging device. The image photographed by the imaging unit 10 is displayed on a display unit 30. The imaging unit 10 is, for example, a digital camera, and is capable of performing a series of processing from photographing, based on a predetermined operation of a user indicating a shutter timing, the user as an object to recording data of the photographed image. An imaging apparatus is implemented by the imaging unit 10 as a digital camera, but may be a compact type or a single-lens reflex type, or may be incorporated in a smart phone.

The imaging unit 10 includes an optical lens unit and an image sensor. The optical lens unit is constituted by lenses for condensing light, such as a focus lens and a zoom lens, in order to photograph an object. The focus lens is for forming an image of the object on the light receiving surface of the image sensor. The zoom lens is for changing the focal length within a certain range. The optical lens unit further includes, as needed, a peripheral circuit for adjusting setting parameters of a focal point, exposure, white balance, and the like.

The image sensor is constituted by a photoelectric conversion element, an analog front end (AFE), and the like. The photoelectric conversion element is constituted by, for example, a complementary metal oxide semiconductor (CMOS) photoelectric conversion element, and the like. The image of the object enters the photoelectric conversion element from the optical lens unit. The photoelectric conversion element photoelectrically converts (photographs) the image of the object, stores image signals for a certain time, and sequentially supplies the stored image signals as analogue signals to the AFE.

The AFE performs various types of signal processing, such as analog/digital (A/D) conversion processing, to the analogue image signals. With the various types of signal processing, digital signals are generated and output as output signals of the imaging unit 10. These output signals of the imaging unit 10 are the data of the photographed image.
(Hardware Configuration of System)

The imaging unit 10 and the evaluation apparatus 20 each includes a central processing unit (CPU), a read only memory (ROM), a random-access memory (RAM), an image processing unit, and a memory. The CPU, the ROM, the RAM, the image processing unit, and the memory are mutually connected through a bus.

The CPU performs various types of processing in accordance with a program recorded in the ROM or loaded from the memory into the RAM. The RAM stores data and the like necessary for the CPU to perform the various types of processing.

The image processing unit is constituted by a digital signal processor (DSP), a video random access memory (VRAM), and the like, and performs various types of image processing to the image data in cooperation with the CPU. For example, the image processing unit performs image processing, such as noise reduction, white balance adjustment, image stabilization, and the like, to the data of the photographed image output from the imaging unit 10.

The memory can be any one of recording media, such as a DRAM, a cash memory, a magnetic disk, an optical disk, a magneto-optical disk, a semiconductor memory, and the like. The memory includes what is read and written through a drive as well as what is connected by the bus. The stored data in the present embodiment is assumed to be temporarily stored in this memory regardless of temporary storage or long-term storage with a non-volatile memory.

The evaluation apparatus 20 is connected with an input/output interface. The evaluation apparatus 20 is connected with a display unit, an input unit, and a communication unit through the input/output interface. The input unit is constituted by various buttons, and receives instruction operation of the user. The communication unit controls communication with other apparatuses through a network including the Internet.

The display unit 30 induces a display apparatus that includes a display screen and displays and reproduces images or videos formed by the image processing unit. The display apparatus can be any display apparatus, such as a monitor, a liquid crystal display, or the like. In the present embodiment, the CPU or the like generates image data to be displayed, and performs image display processing on the display screen through the image processing unit. In the following description, when the term "to display" is simply used, display processing including the above function can be performed.

The evaluation apparatus 20 has the above configuration, but its functional configuration is to be described later. The functional configuration is functionally implemented by the CPU, the ROM, the RAM, the image processing unit, and the memory cooperating with each other. The functions of these units are module configurations provided by electronic circuits or programs, and the programs are stored in the ROM and executed by the CPU appropriately loading them and cooperating with the other units.
(Head Image and Surface-Reflected Light)

Figure 2:
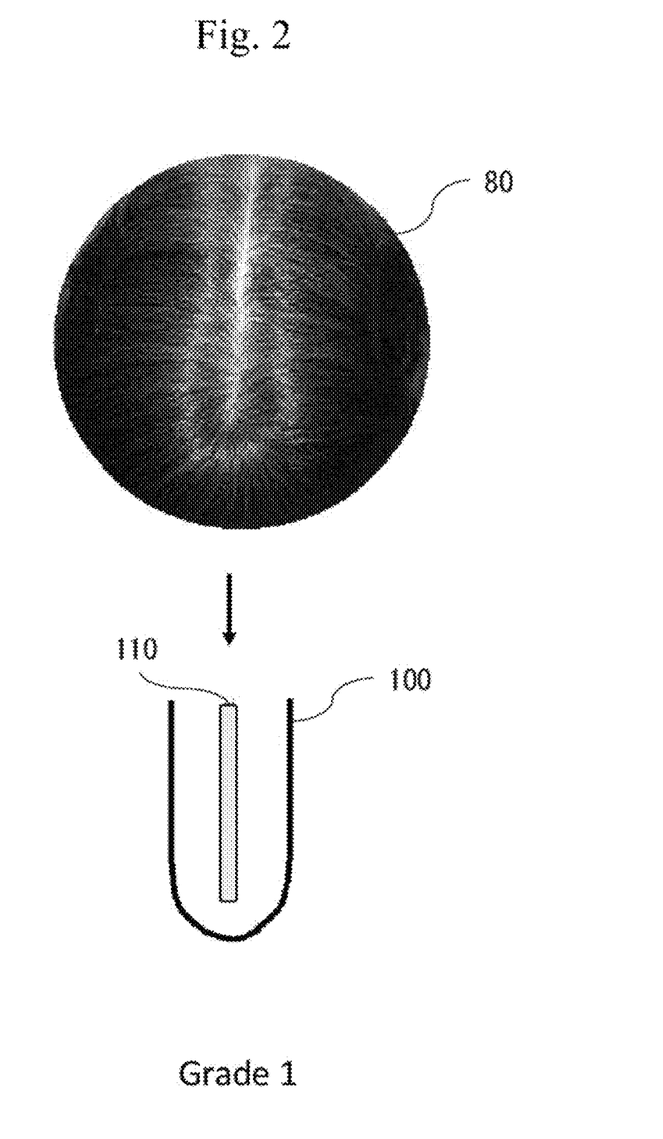
FIG. 2 is a diagram showing a first example of a hair image and an outline of surface-reflected light.

FIG. 2 shows a first example of a hair image and an outline of surface-reflected light. An example of an image of the head H photographed by the imaging unit 10 is a head image 80. In the head image 80, surface-reflected light 100 is clearly formed in parallel to a partline 110 of the hair from the frontal region to the parietal region, and has a U shape at the periphery of the hair whorl. This first example shows a normal condition, that is, hair loss does not advance, and other examples are described using the image of the first example as a reference.

Figure 3:
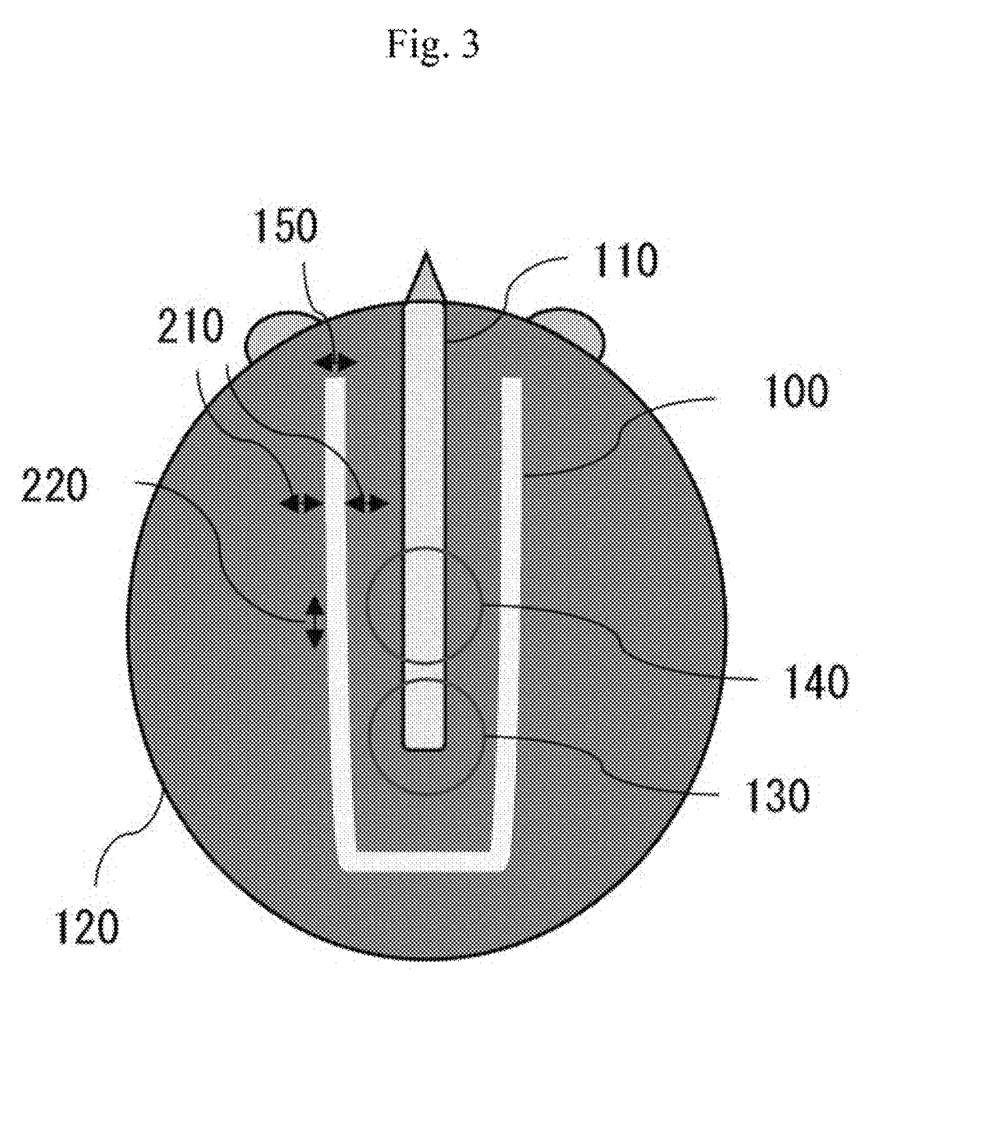
FIG. 3 is a diagram showing the first example of detailed portions of the hair image and the surface-reflected light.

FIG. 3 shows the first example of detailed portions of the hair image and the surface-reflected light. In the head image 80 shown in FIG. 2, the surface-reflected light 100, the partline 110, and the other portions are more detailedly described. The surface-reflected light 100 on the hair is shining light reflected on the cuticle surface of the hair. In the following, the surface-reflected light 100 or surface-reflected light in other grades are examples of reflection images in which surface-reflected light is formed, and are described without the description as images for the sake of explanation. The partline 110 is exposed scalp by mainly parting the hair at the center.

The surface-reflected light 100 and the partline 110 are formed on a head 120. The partline 110 is preferably formed mainly at the center of the head 120 by passing through the parietal region 140 that is the highest point of the head 120, but may be formed at any region other than the center as long as the partline 110 and the surface-reflected light 100 can be certainly photographed by the imaging unit 10. A hair whorl 130 includes both an anatomical hair whorl and the end of the partline 110 at the back of the head.

In the head image 80 of FIG. 2, the surface-reflected light 100 is formed in substantially parallel to the partline 110 as abstractly expressed in FIG. 3. In addition, the surface-reflected light has a sufficient light width 150. The light width 150 is different from individual and is not fixed, but is about 1 to 2 cm. Naturally, the surface-reflected light 100 is not exactly parallel and can be slightly shifted to the right or the left. However, if a shift 210 is within a range having the same width as the light width 150, this image falls under Grade 1 shown in FIGS. 2 and 3. This Grade 1 indicates a normal condition in which hair loss does not advance as described above. Note that, the shift 210 can be shifted to the outer side of a U shape 100 and also shifted to the midline side as shown in FIG. 3.

In the present embodiment, the image photographed by the imaging unit 10 is analyzed and evaluated as described above to determine a grade. The analysis evaluation processing is performed by the evaluation apparatus 20. The grade of the head image 80 is determined as the result of the analysis evaluation. The functional configuration of the evaluation apparatus 20 is described below.
(Functional Configuration of Evaluation Apparatus 20)

Figure 4:
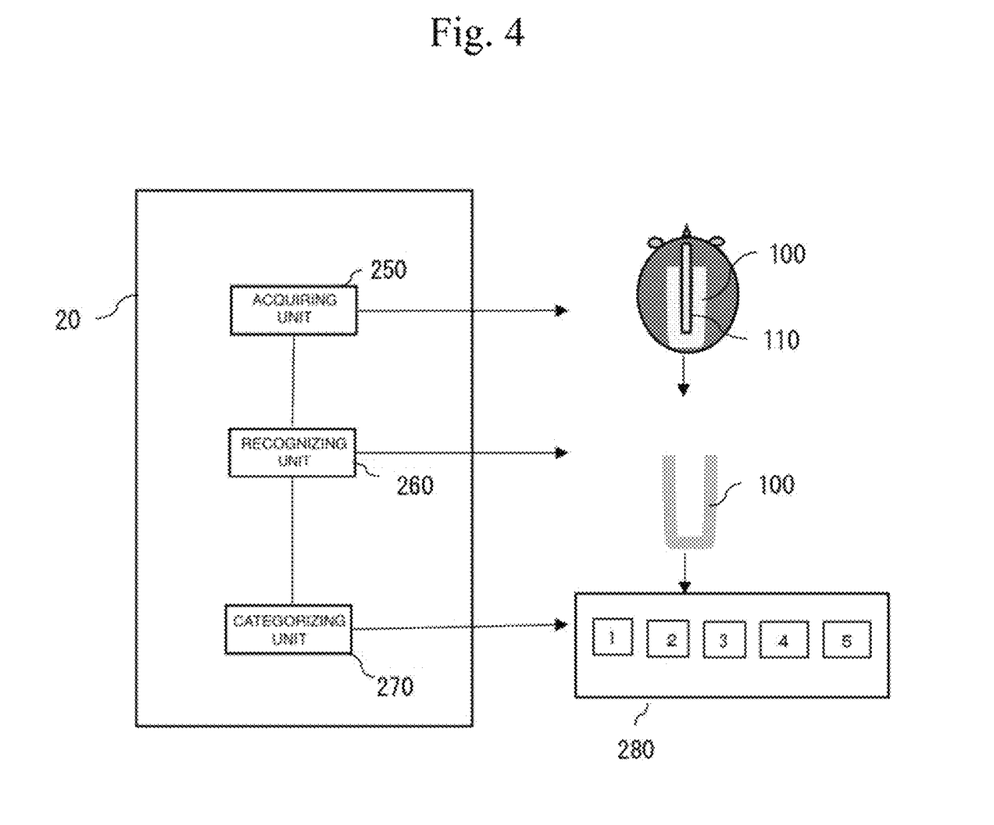
FIG. 4 is a diagram showing a functional configuration in the present embodiment.

FIG. 4 shows the functional configuration of the evaluation apparatus according to the present embodiment. The evaluation apparatus 20 includes an acquiring unit 250, a recognizing unit 260, and a categorizing unit 270. The acquiring unit 250 acquires the head image 80 obtained by photographing the whole of the head of the subject including the hair H and the periphery of the hair H where hair does not appear.

The recognizing unit 260 recognizes, from an image 100 in which the surface-reflected light in the head image 80 is formed, the shape of the U-shaped surface-reflected light formed from the frontal region to the periphery of the hair whorl. Since the hair H is basically black or a color as hair including color-treated hair, the recognizing unit 260 extracts a U-shaped portion distinguished by the color of the hair. The portion distinguished by the color of the hair includes the surface-reflected light 100 and the partline 110. However, since these differ in color and the surface-reflected light 100 is formed in a U shape and the partline 110 is formed in a straight line, these are distinguished by focusing the feature information. As the result of the distinguishing, the recognizing unit 260 recognizes the image 100 of the surface-reflected light, and especially the U shape.

The categorizing unit 270 determines the shift degree of the U shape 100 with image processing, and categorizes the degree as one of a plurality of stages 280. The shift degree indicates how much the shape is shifted compared to the normal condition, that is, the condition of the surface-reflected light 100 categorized as Grade 1. In the image processing in this case, for example, a surface-reflected light image in the normal condition is extracted based on the shape of the head from internal storage data to determine a matching degree and an image shifting degree, and how the shape is shifted from the normal condition in Grade is determined.

FIGS. 2 and 3 show that the U shape 100 is normal and in Grade 1, but an actual U shape does not have such a perfect U shape, and this U shape is gradually shifted and deforms as the hair loss symptom advances. Thus, the U shape is categorized as one of Grades 2 to 5 according to a shift degree and a deformation degree.

The definition of shift degrees is stored as feature quantities in advance. The categorizing unit 270 obtains the feature quantity of the shape recognized by the recognizing unit 260 with the image processing, compares the feature quantity with the stored feature quantities, and determines that the acquired head image 80 falls under which one of Grades 1 to 5. The feature quantity can be, for example, data based on the coordinate value of the U shape 100. For example, 10 points are extracted from points constituting the U shape 100, and the point coordinates can be the feature quantity. The point coordinates as the feature quantity can be determined and categorized based on the difference from the symptom in the normal condition. Naturally, this difference value can be used as the feature quantity. Here, the features and outlines of Grade 1 to 5 are described in order to perform categorizing.

[Outline of Grade Categorizing]

The stages 280 into which the categorizing unit 270 categorizes the image are the following five stages. These five stages are described below.

Grade 1

If the hair has a certain thickness or more, and the thickness does not extremely vary, the surface-reflected light 100 having a certain length regularly clearly appears in substantially parallel to the partline 110 and turns at the periphery of the hair whorl 130 into a U shape. A shift width 210 of the surface-reflected light to the outer side or the midline side is less than the light width 150 of the surface-reflected light, which is shown in FIGS. 2 and 3 as described above.

Grade 2

When the volume of the hair at a certain region is reduced due to a decrease in hair diameter or hair density, the peak of the thickness of the hair at the region is lower than the periphery of the region, and the shape of the surface-reflected light deforms according to the change. Thus, the surface-reflected light appears irregularly. The belt of the surface-reflected light is clear and appears in substantially parallel to the partline 110, and turns at the periphery of the hair whorl 130 into a U shape. The shift width 210 of the surface-reflected light to the outer side or the midline side is equal to or more than the light width 150 of the surface-reflected light and less than twice the light width 150.

Grade 3

When the volume of the hair at the certain region is further reduced compared to Grade 2, or when a range where the volume of the hair is reduced is increased compared to Grade 2, the partline is rarely opened, but the peak of the thickness of the hair is much lower than the periphery, and the shape of the surface-reflected light deforms according to the change. Thus, the surface-reflected light appears but is far from the state of being parallel to the partline 110. The belt of the surface-reflected light is clear, but is shifted to the outer side or the midline side by a distance equal to or more than twice the light width 150 of the surface-reflected light from the state of being parallel to the partline 110.

Grade 4

When the volume of the hair at the certain region is further reduced compared to Grade 3, or when the range where the volume of the hair is lowered is increased compared to Grade 3, at the region where the thickness of the hair is lowered, the partline is slightly opened, but the surface-reflected light becomes unclear, and the continuity of the surface-reflected light is unclear. The belt of the surface-reflected light is weakened, and unclear portions or discontinued portions having a length equal to or more than the width of the belt 150 of the surface-reflected light appear in an anteroposterior direction 220 of the head or in the curve at the periphery of the hair whorl.

Grade 5

When the volume of the hair at the certain region is further reduced compared to Grade 4, or when the range where the volume of the hair is lowered is increased compared to Grade 4, at the region where the thickness of the hair is lowered, the partline is appreciably opened, and the belt of the surface-reflected light is unclear and discontinuous. The surface-reflected light does not have a belt-like shape, but is a group of lines of light.

Figure 5:
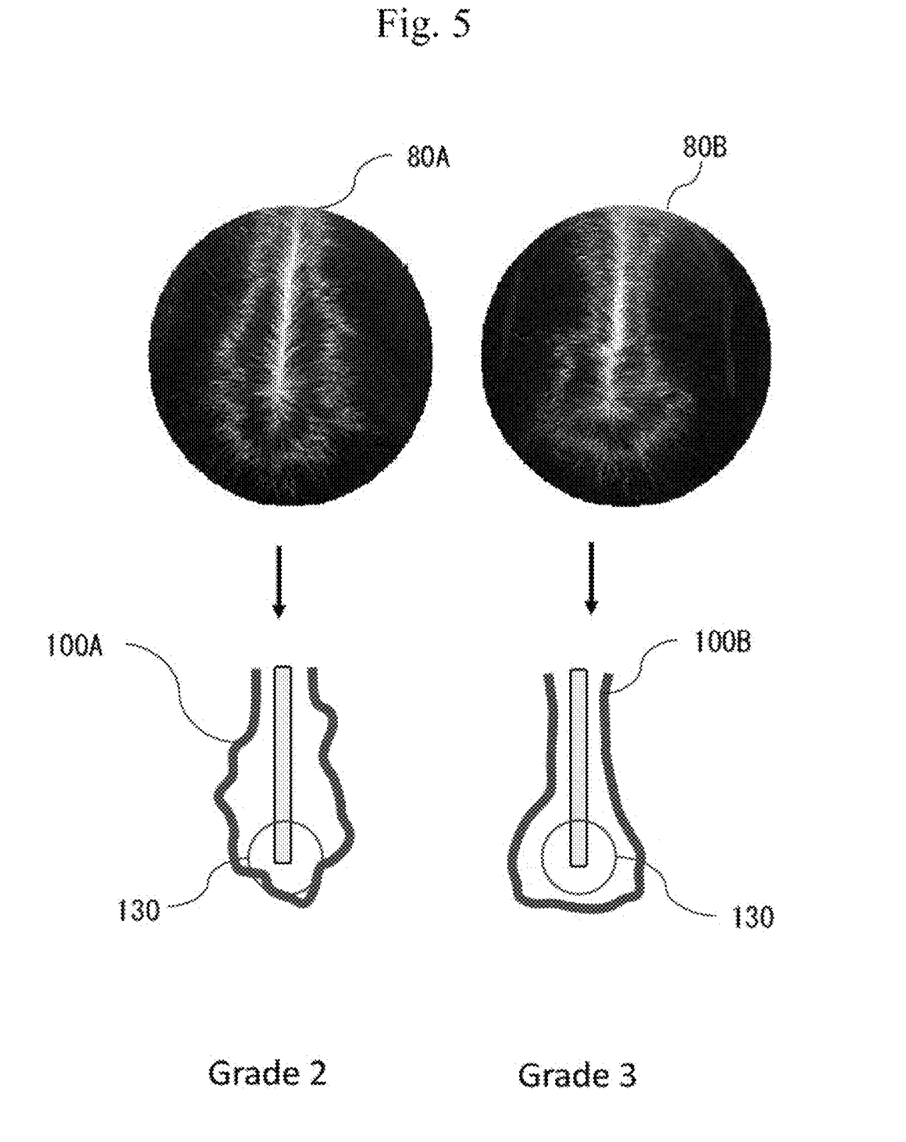
FIG. 5 is a diagram showing a second example of a hair image and an outline of surface-reflected light.
Figure 6:
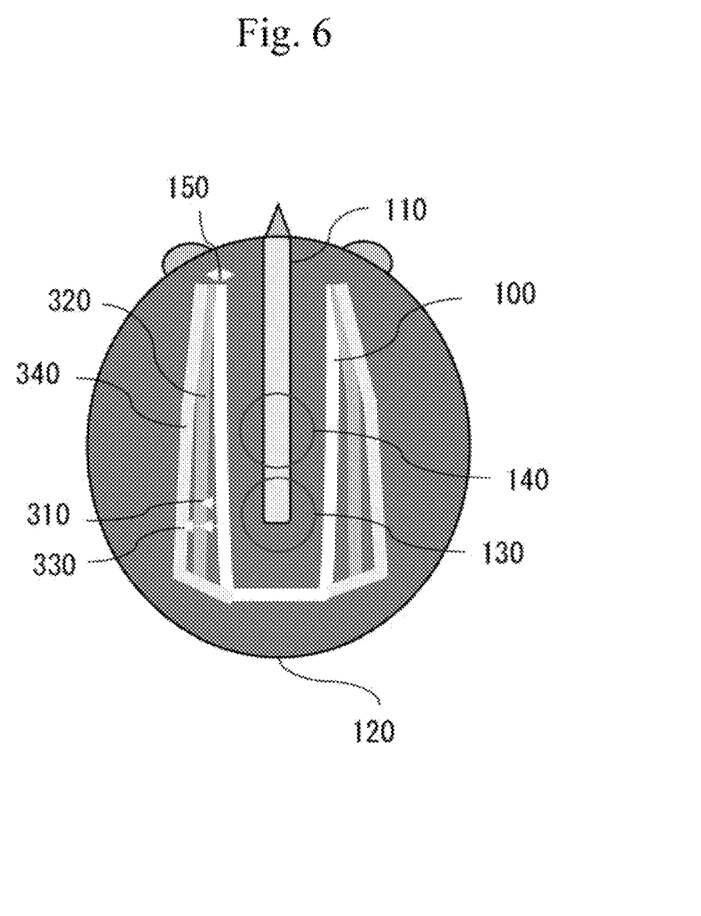
FIG. 6 is a diagram showing the second example of detailed portions of the hair image and the surface-reflected light.

Since the outlines of Grade 1 to 5 have been described, each grade is detailedly described with reference to images and the drawings. FIG. 5 shows a second example of a hair image and the outline of surface-reflected light. FIG. 6 shows the second example of detailed portions of the hair image and the surface-reflected light.

FIG. 5 shows images of the head H in Grades 2 and 3 photographed by the imaging unit 10 and corresponding to the head images 80. A left head image 80A is in Grade 2, and a right head image 80B is in Grade 3. In contrast to Grade 1 that is the normal condition in which hair loss does not advance, each image shows that hair loss advances to some extent. The images are categorized as Grades 2 and 3 at an early stage in which the U shape begins to lose parallelism to the partline.

In the head image 80A, the surface-reflected light is clearly formed from the parietal region 140 to the hair whorl 130 and has a U shape. Abstractly, surface-reflected light 100A and the partline 110 of the hair are formed. The head image 80B also has a U shape, and surface-reflected light 100B and the partline 110 of the hair are formed.

The head image 80A and the surface-reflected light 100A fall under Grade 2. The surface-reflected light has a wave-like shape, and is formed into a U shape that bulges at the periphery of the hair whorl 130 compared to the frontal region, but keeps a shape in substantially parallel to the partline 110.

On the other hand, the head image 80B and the surface-reflected light 100B fall under Grade 3. The surface-reflected light formed into a U shape bulges toward the periphery of the hair whorl 130, and hardly keeps a parallel shape.

FIG. 6 shows the second example of detailed portions of the hair image and the surface-reflected light. FIG. 6 is for describing the portions of the head images 80A and 80B shown in FIG. 5 more detailedly, and corresponds to FIG. 3. FIG. 6 is different from FIG. 3 in the surface-reflected light 100 formed by irradiation with light.

In FIG. 6, the surface-reflected light 100 is overlapped for the sake of explanation. In Grade 2 shown as the head image 80A, surface-reflected light 320 having a shift 310 to the outer side compared to the surface-reflected light 100 is formed. In the example of FIGS. 5 and 6, the surface-reflected light 320 is partially parallel to the partline to some extent, but, at the periphery of the hair whorl 130, has the shift 310 to the outer side by the distance equal to or more than the light width 150 described in FIG. 3. As described, if the surface-reflected light from the frontal region to the periphery of the hair whorl is shifted from the shape parallel to the partline 110 to an outer side 310 or the midline side by a distance equal to or more than the light width 150, the image is classified as Grade 2. When the shift to the outer side 310 or the midline side has a distance less than the light width 150, the image is classified as Grade 1.

In Grade 3 shown as the head image 80B, surface-reflected light 340 has a larger shift 330 to the outer side compared to the surface-reflected light 320. As described, when the surface-reflected light is shifted from the shape parallel to the partline 110 to an outer side 330 or the midline side by the distance equal to or more than twice the light width 150 described in FIG. 3, the image is classified as Grade 3.

In the example of FIGS. 5 and 6, the surface-reflected light 340 partially maintains parallelism at the forehead, but, at the periphery of the hair whorl 130, has the shift 330 from the shape parallel to the partline 110 to the outer side by the distance equal to or more than twice the light width 150. As described, the image is classified as Grade 2 when the surface-reflected light is shifted from the shape parallel to the partline 110 to an outer side 310 or the midline side by the distance equal to or more than the light width 150 and less than twice the light width 150, and the image is classified as Grade 3 when the surface-reflected light is shifted by the distance equal to or more than twice the light width 150.

The surface-reflected light 320 and the surface-reflected light 340 are shown by being overlapped for the sake of explanation, but the surface-reflected light 320 appears only in Grade 2, and the surface-reflected light 340 appears only in Grade 3. The surface-reflected light 100 does not appear in both grades.

Figure 7:
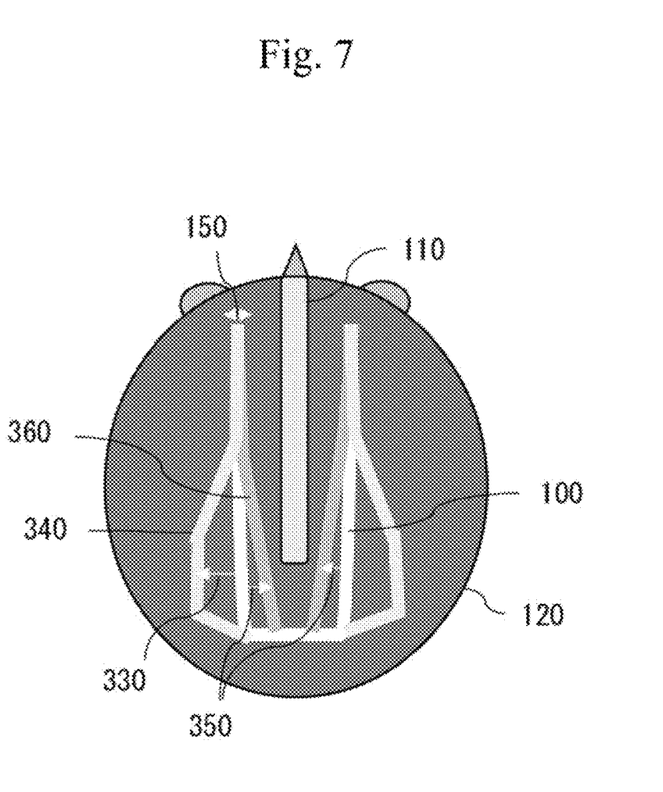
FIG. 7 is a diagram showing a third example of detailed portions of a hair image and surface-reflected light.

FIG. 7 shows a third example of detailed portions of a hair image and surface-reflected light. FIG. 6 shows that the surface-reflected light 100 in Grades 2 and 3 is shifted to the outer side, but the shift direction in Grades 2 and 3 is not limited to the outer sides 310 and 330, and includes a shift to a midline side 350 as shown in FIG. 7.

The shift to the outer side 330 in Grade 3 has been shown in FIG. 6 and described, and a shift to the midline side 350 is shown in FIG. 7. As the result of occurring a shift 350 to the midline side, surface-reflected light 360 is formed. The surface-reflected light 360 is shifted to the midline side by the distance equal to or more than twice the light width 150, similarly to the surface-reflected light 340.

Figure 8:
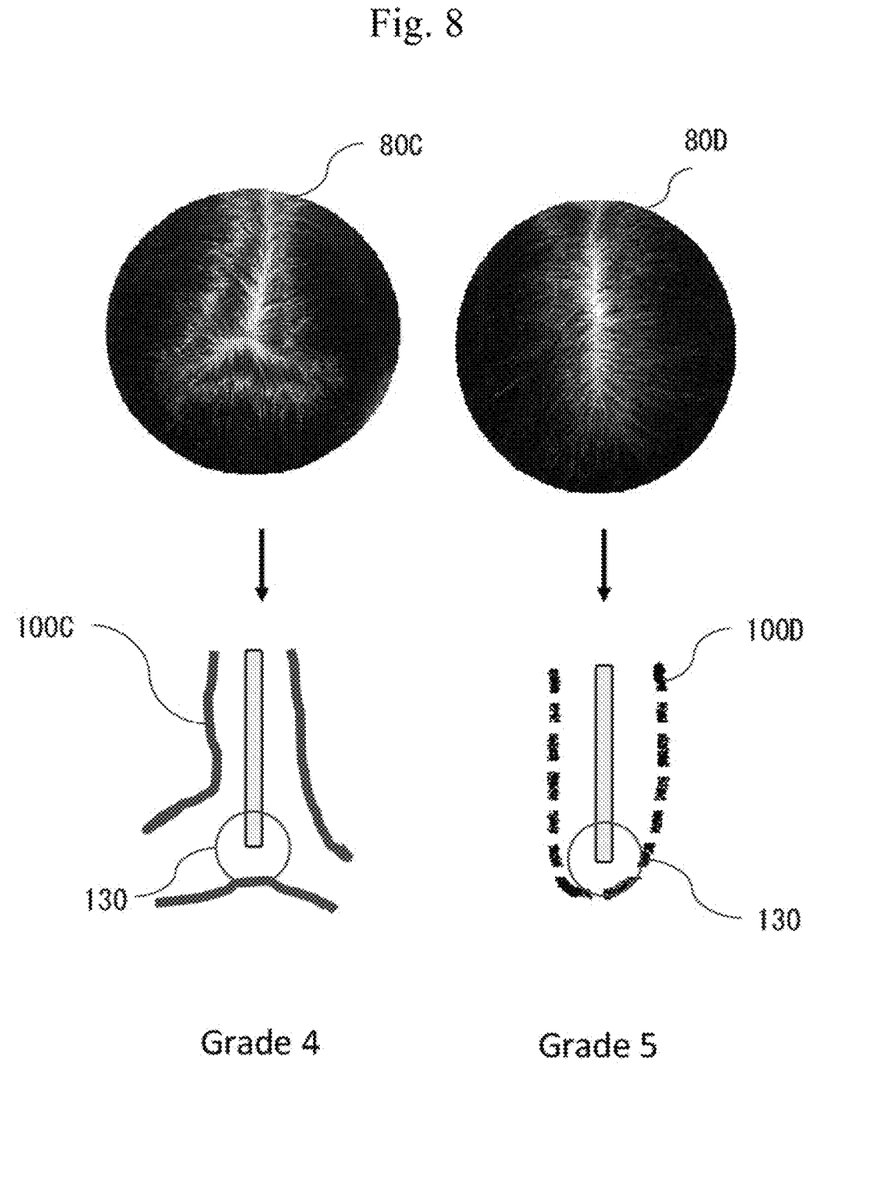
FIG. 8 is a diagram showing the third example of the hair image and an outline of the surface-reflected light
Figure 9:
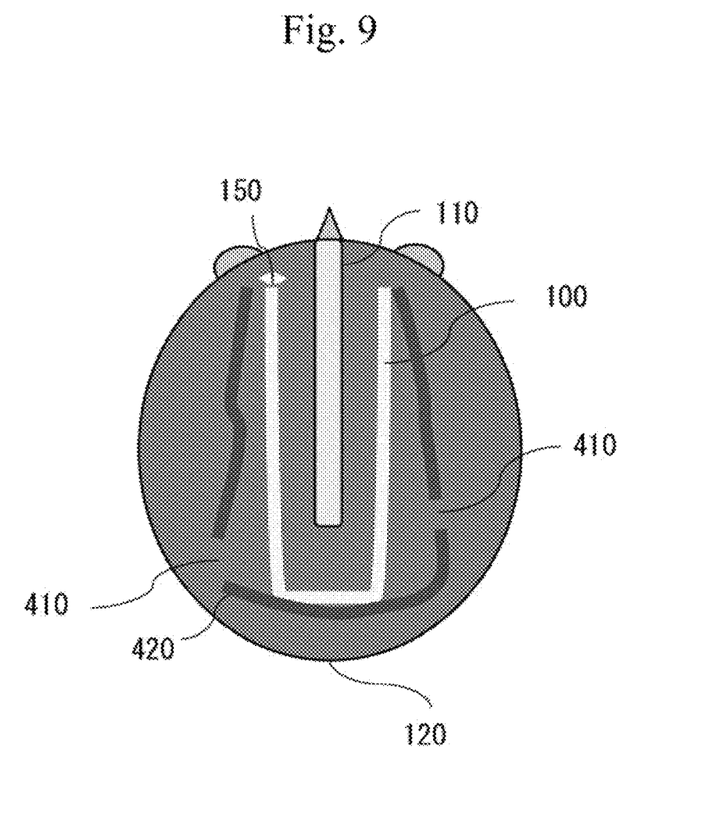
FIG. 9 is a diagram showing a fourth example of detailed portions of a hair image and surface-reflected light.

FIG. 8 shows the third example of the hair image and the outline of the surface-reflected light. FIG. 9 shows a fourth example of detailed portions of a hair image and surface-reflected light. FIG. 8 shows images of the head H in Grades 4 and 5 photographed by the imaging unit 10 and corresponding to the head images 80. A left head image 80C is in Grade 4, and a right head image 80D is in Grade 5. The images show the stage in which the thickness of the hair is further weakened and hair loss advances, and the images are categorized as Grades 4 and 5 at an advanced stage in which the U shape begins to be unclear.

In the head image 80C, surface-reflected light 100C is formed. In the head image 80D, surface-reflected light 100D is similarly formed. The head image 80C and the surface-reflected light 100C fall under Grade 4. Meanwhile, the head image 80D and the surface-reflected light 100D fall under Grade 5.

FIG. 9 shows the fourth example of detailed portions of the hair image and the surface-reflected light. FIG. 9 is for describing the portions of the head image 80C shown in FIG. 8 more detailedly, and corresponds to FIG. 3. FIG. 9 is different from FIG. 3 in the surface-reflected light 100. In FIG. 9, the surface-reflected light 100 is overlapped for the sake of explanation. In Grade 4 shown as the head image 80C, surface-reflected light 420 having a discontinuous shape is formed due to chasms 410 generated by the reduced thickness of the hair compared to the surface-reflected light 100, 100A, and 100B.

The feature of Grade 4 is that the chasms 410 are generated. Although fine gaps are generated in the surface-reflected light in Grades 1 to 3, those gaps only have a length less than the light width 150 in anteroposterior direction 220 in FIG. 3. When the chasm 410 has a length equal to or more than the light width 150, the image is classified as Grade 4. The light width 150 has been described based on the surface-reflected light 100, but may be based on the surface-reflected light 420, and these have a substantially similar width.

Figure 10:
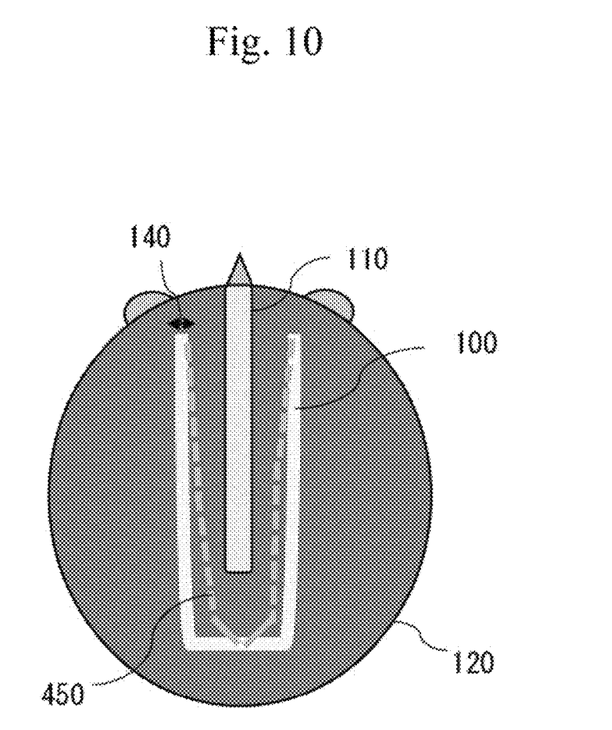
FIG. 10 is a diagram showing a fifth example of detailed portions of a hair image and surface-reflected light.

FIG. 10 shows a fifth example of detailed portions of a hair image and surface-reflected light. FIG. 10 is for describing the portions of the head image 80D shown in FIG. 8 more detailedly, and corresponds to FIG. 3. FIG. 10 is different from FIG. 3 in the surface-reflected light 100.

In Grade 5 shown as the head image 80D, the surface-reflected light 450 shifted to the midline side compared to the surface-reflected light 100 is formed toward the hair whorl. The surface-reflected light 450 does not have a belt-like shape but has an intermittent linear shape. The surface-reflected light in Grades 1 to 4 can be recognized as a planar shape to some extent, but the surface-reflected light in Grade 5 has a linear shape. As the difference between the linear shape and the planar shape, the shape is linear when the surface-reflected light 450 being parallel 220 or orthogonal 210 to the partline 110 has a length or a width half or less than the light width 150, and the shape is planer when the surface-reflected light 450 has a width half or more than the light width 150. Especially, the condition in which the surface-reflected light 450 cannot be visually recognized as a planar shape and becomes a group of discontinuous lines like legs of a centipede is the typical condition in Grade 5.

In FIG. 9, the surface-reflected light 100 and the surface-reflected light 420 are shown by being overlapped for the sake of explanation, but the surface-reflected light 420 appears only in Grade 4. In FIG. 10, the surface-reflected light 100 and the surface-reflected light 450 are shown by being overlapped for the sake of explanation, but the surface-reflected light 450 appears only in Grade 5.

(Comparison Experiment Between Categorizing Using GP According to the Present Invention and FPHL-SI, and Verification Experiment of Practical Utility)

The categorizing unit 270 determines the hair loss stage of a patient with image processing at an early FPHL stage by categorizing a photographed hair image as one of five stages divided with the above concept. Here, whether categorizing images into five stages based on the features of the images is suitable for determining the hair loss stage of the patient is verified by comparing the categorizing with the Female pattern hair loss-severity index (FPHL-SI).

In addition, whether this categorizing is understood by patients and has a practical utility is verified with consistency rates between categorizing of hair images and volunteers' understanding about the progress evaluation. Specifically, the FPHL-SIs of hair images of 114 persons categorized in accordance with the conditions are calculated. Then, the hair images are categorized by the volunteers in accordance with the conditions, and the obtained results are compared.

If the grade categorizing using GPs according to the present invention and the FPHL-SIs basically have a correspondence relation in the experiment results, the result of the categorizing by a parting unit 270 basically indicates the hair loss stage of the patient, and patients can easily understand as the consistency rate of the volunteer to the evaluation categorizing is high.

EXAMPLES

Method

The retrospective chart for the women who had a medical check-up at Bona Dea Clinic from July 2012 to November 2016 for the first time and diagnosed as early FPHL was reviewed. The diagnosis as early FPHL was determined based on their medical histories, physical test observations, blood test observations, scope images, and GPs.

Regarding the GPs, the photographs were taken every time with the same procedure as follows. A patient who came to the clinic with no styling agent sat raising the head so that the parietal region and the hair whorl were positioned at the front and the center (FIG. 1). The photograph of the whole of the head was taken by an internal flash camera. The subjects of this experiment were the early FPHL patients who fully satisfied the following three conditions. The three conditions were that the patient had a follow-up observation period of six months or longer, that the patient had all data necessary for this study, and that the GP had substantially the same luminance of the background. The number of the patients satisfying these conditions were 114.

All the GPs of the 114 patients obtained during the treatment progress were classified into five stages based on the change in the shape of the surface-reflected light formed on the hair as described above. Then, the GPs having the highest grade value and the lowest grade value were extracted for each patient. Next, the FPHL-SIs at a time close to the time when the extracted photographs were taken were calculated.

The evaluation items for the FPHL-SI were four of hair shedding, midline hair density, hair diameter variation, and the difference of a hair included a hair follicle unit according to positions, as disclosed in Non-Patent Literature 4.

Losing less than 200 hairs per day or negative in a pull test was set as 0 point, positive in a pull test was set as 2 points. Regarding the midline hair density, Sinclair Midline hair density Grade 1, in which an obvious decrease in hair density was not observed clinically although a patient complained excessive hair loss and loss of hair volume, was set as 0 point, and Grade 2, in which obvious hair loss was observed clinically although it was mild, was set as 4 points. In Trichoscopy, an image in which varieties of the hair diameters less than 0% was set as 0 point, an image having varieties of 20% or more was set as 5 points. In addition, no difference of a hair included a hair follicle unit between the forehead and the back of the head was set as 0 point, the difference of 25% or more was set as 1 point, and the difference of 50% or more was set as 2 points.

After the FPHL-SIs were calculated for the GPs, the FPHL-SIs were grouped into the five stages according to the present invention, and the average value of the FPHL-SIs for each group was calculated. Then, the relevancy between the grades according to the present invention and the FPHL-SI values was studied statistically.

Two photographs extracted for each patient as described above were randomly allocated to one side of a slide. Three volunteers (one man and two women) were given explanation of the grade categorizing according to the present invention, divided 114 examples of (228) photographs into the grades, and determined which photograph of the two seemed milder. Then, the consistency rates of the grade evaluation and the progress comparison between the inventor and the volunteers were analyzed.

[Result]

1. Distribution of GPs

Among the 228 GPs, 30 GPs were in Grade 1, 64 GPs were in Grade 2, 61 GPs were in Grade 3, 50 GPs were in Grade 4, and 23 GPs were in Grade 5.

Figure 11:
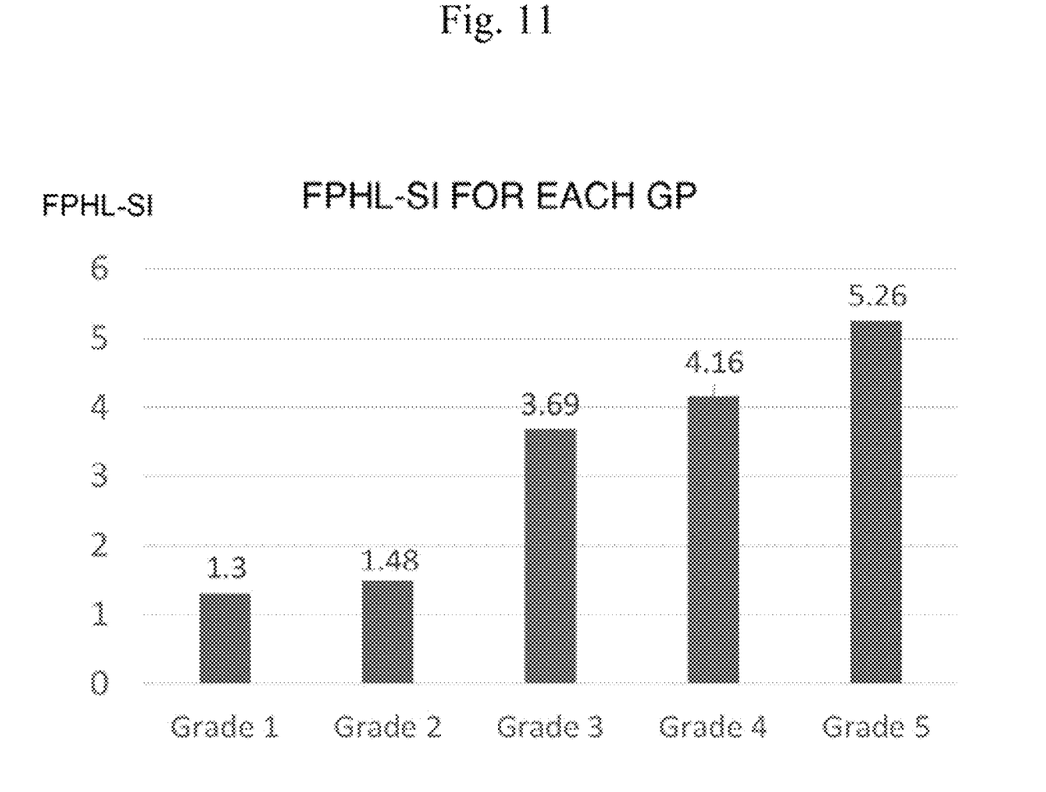
FIG. 11 is a graph showing values of FPHL-SI for each GP.

2. FIG. 11 shows FPHL-SI values (the average value and the standard error) by relevancy grades between the grades described in the present embodiment and the FPHL-SI values. The FPHL-SI index values tended to be high in the groups in higher grades according to the present invention. However, since the FPHL-SI values were not normally distributed, the evaluation for relevancy using correlation coefficients could not be performed statistically.

The FPHL-SI has been proposed by Harris et al. in 2016 as a new evaluation method for FPHL severity including early FPHL. This severity evaluation method disclosed in Non-Patent Literature 4 covers FPHL symptoms with scoring, and a medical doctor can evaluate the condition of a patient objectively. In the present embodiment, FPHL-SI values tended to be high as the GP grade becomes higher, but statistically significant relevancy was not shown (FIG. 11). The reason is because the FPHL-SI values of the subjects in the present embodiment were not normally distributed; most of the values were distributed to 0 and 5 although the values were distributed to 0 to 11. In addition, the reason can be because the evaluation for early FPHL was not focused in the FPHL-SI, and all the grades in FPHL were evaluated as numerical values.

3. Consistency Rate with Volunteer

Regarding the consistency rate of the GP evaluation categorizing according to the present invention, 57% (131/228) of photographs were matched between two or more volunteers and the author, 41% (93/228) of photographs were matched between one volunteer and the author, and 2% (4/228) of photographs were not matched (Table 1).

Regarding the consistency rate of the progress comparison, 97% (111/114 examples) of determination was matched between two or more volunteers and the author, 2% (3/114 cases) of determination was matched between one volunteer and the author, and 1% (1/114 examples) of determination was not matched (Table 1: consistency rate of evaluation between inventor and three volunteers).

TABLE 1

|  | 2 or more out of 3 persons | 1 out of 3 persons | No matching |
|---|---|---|---|
| Grade evaluation (photograph) | 57% (131) | 41% (93) | 2% (4) |
| Progress evaluation (case) | 97% (111) | 2% (2) | 1% (1) |

As the result of studying whether the evaluation of treatment progress that was easily understood by patients was possible with the five-grade classification according to the present invention, the experiment for the embodiment with volunteers showed the possibility that those who were not accustomed to seeing GPs would easily understand the progress (Table 1).

As described above, by setting evaluation criteria based on the shape of surface-reflected light, the present embodiment has shown a possibility that treatment progress can be evaluated with GPs even in early FPHL that is difficult to evaluate objectively. By providing 5-stage categorizing based on GPs with the categorizing unit 270, it is possible to easily diagnose early hair loss in a short time.

The present invention has been described with the embodiment, but the technical scope of the present invention is not limited to the range described in the embodiment. It is obvious for those who are skilled in the art to make various changes and improvements to the above embodiment. It is further obvious, from the description of the scope of claims, that modifications after such changes and improvements can be included in the technical scope of the present invention. In addition, it is obvious that early evaluation for hair loss other than female pattern hair loss (FPHL) is possible from the description of the scope of claims.

REFERENCE SIGNS LIST

H Hair
P Subject
10 Imaging unit
20 Evaluation apparatus
80 Head image
100 Surface-reflected light
110 Partline
120 Head
130 Hair whorl
140 Parietal region
150 Light width
250 Acquiring unit
260 Recognizing unit
270 Categorizing unit
320 Surface-reflected light
340 Surface-reflected light
420 Surface-reflected light
450 Surface-reflected light

The invention claimed is:

1. A head-image evaluation apparatus comprising:
   an acquiring unit configured to acquire a head image obtained by photographing hair of a subject;
   a recognizing unit configured to recognize surface reflected light formed in a U shape on the hair at a periphery of a hair whorl and in a belt-like shape on the hair along a partline at a frontal region and at a parietal region, the surface reflected light being included in the head image; and
   a categorizing unit configured to determine a stage indicating a change in volume of the hair depending on a position where the surface reflected light is formed at the frontal region and at the parietal region.

2. The head-image evaluation apparatus according to claim 1, wherein the categorizing unit is configured to determine the stage depending on a shift degree of the position from a predetermined normal condition of the surface reflected light at the frontal region, the parietal region, and the periphery of the hair whorl.

3. The head-image evaluation apparatus according to claim 1, wherein
   the categorizing unit is configured to determine any one of a normal stage, an early stage, and an advanced stage,
   the normal stage is determined when the surface-reflected light forms a parallel shape having a fixed space from the partline at the frontal region and at the parietal region and a regulated U shape at the periphery of the hair whorl,
   the early stage is determined when the parallel shape at the frontal region and at the parietal region and the U shape at the periphery of the hair whorl deform, and
   the advanced stage is determined when the parallel shape at the frontal region and at the parietal region and the U shape of the surface-reflected light at the periphery of the hair whorl becomes unclear over a certain range or wider.

4. The head-image evaluation apparatus according to claim 1, wherein
   the categorizing unit is configured to determine any one of a first stage, a second stage, a third stage, a fourth stage, and a fifth stage,
   the first stage is determined when the surface-reflected light forms a shape parallel to the partline from the frontal region to the parietal region and a regulated U shape at the periphery of the hair whorl,
   the second stage is determined when the parallel shape at the frontal region and the parietal region and the U shape at the periphery of the hair whorl partially have a shift,
   the distortion degree is categorized as the third stage is determined when the surface-reflected light having the parallel shape at the frontal region and the parietal region and a curved shape at the periphery of the hair whorl has a remarkable shift at the periphery of the hair whorl,
   the fourth stage is determined when the surface-reflected light at the periphery of the hair whorl becomes partially unclear, and
   the fifth stage is determined when the surface-reflected light at the periphery of the hair whorl becomes entirely unclear.

* * * * *